United States Patent
Zhou et al.

(10) Patent No.: US 8,735,605 B2
(45) Date of Patent: May 27, 2014

(54) HETEROCYCLIC QUINOID THIOPHENE ORGANIC PHOTOELECTRIC MATERIAL, PREPARATION METHOD AND APPLICATION THEREOF

(75) Inventors: Mingjie Zhou, Shenzhen (CN); Jie Huang, Shenzhen (CN); Hui Liu, Shenzhen (CN)

(73) Assignee: Ocean's King Lighting Science & Technology Co., Ltd., Guangdong (CN)

( * ) Notice: Subject to any disclaimer, the term of this patent is extended or adjusted under 35 U.S.C. 154(b) by 113 days.

(21) Appl. No.: 13/575,699

(22) PCT Filed: Jan. 30, 2010

(86) PCT No.: PCT/CN2010/070438
§ 371 (c)(1),
(2), (4) Date: Sep. 10, 2012

(87) PCT Pub. No.: WO2011/091609
PCT Pub. Date: Aug. 4, 2011

(65) Prior Publication Data
US 2013/0005989 A1 Jan. 3, 2013

(51) Int. Cl.
*C07D 333/78* (2006.01)
*C07F 7/08* (2006.01)

(52) U.S. Cl.
CPC ................................ *C07F 7/0818* (2013.01)
USPC ............................................................. 549/4

(58) Field of Classification Search
USPC ............................................................. 549/4
See application file for complete search history.

(56) References Cited

FOREIGN PATENT DOCUMENTS

| CN | 101389634 A | * | 3/2009 |
| JP | 2006-278682 A | * | 10/2006 |
| WO | 2009/115413 A2 | * | 9/2009 |

* cited by examiner

*Primary Examiner* — Taofiq A Solola
(74) *Attorney, Agent, or Firm* — Rosenberg, Klein & Lee

(57) ABSTRACT

A heterocyclic quinoid thiophene organic photoelectric material, which comprises a compound represented by formula (1), in which $R_1$, $R_2$, $R_5$ and $R_6$, which may be identical or different, are H or $C_1$-$C_{20}$ alkyl or alkoxyl; $R_3$ and $R_4$, which may be identical or different, are $C_1$-$C_{20}$ alkyl or alkoxyl; a and b, which may be identical or different, are integer of 1-12; X is Si or C. A preparation method of said heterocyclic quinoid thiophene organic photoelectric material and the use thereof are also disclosed.

13 Claims, 4 Drawing Sheets

(1)

HETEROCYCLIC QUINOID THIOPHENE ORGANIC PHOTOELECTRIC MATERIAL, PREPARATION METHOD AND APPLICATION THEREOF

FIELD OF THE INVENTION

The present disclosure relates to organic materials, and more particularly relates to a heterocyclic quinoid thiophene organic photoelectric material, preparation method and application thereof.

BACKGROUND OF THE INVENTION

At present, the world economy is mainly built on fossil energies, such as coal, petroleum, natural gas and so on. However, these non-renewable fossil energies are going to dry up day by day. Especially since the beginning of 21st century, global energy problems followed by problems of environmental pollution and climate warming are getting worse and worse, and thus have drew more and more attention. Solar energy is known as one of the most hopeful renewable energies for its advantages of universal existence, no pollution, clean, safe, convenient acquiring and so on. Therefore, solar cell which can transform solar energy into electric energy directly is becoming a practical and effective way to use the solar energy. However, conventional commercial solar batteries are limited only to inorganic solar batteries with silica-bases which are much expensive and beyond people's general acceptable degree, thus the application range of the commercial solar batteries is greatly limited. In order to reduce the cost and expand the application range of the solar batteries, people are trying to seek new solar cell materials since a long time ago.

Compared with inorganic semiconductor materials with limited recourses, expensive price, poisonous composition, complicate preparation technology, high cost and so on, organic solar batteries which are new kinds of solar batteries have incomparable advantages, such as wide raw material recourses, structural diversity and controllable property, low cost, safe and no pollution, simple manufacture technology, light weight of products, may be made into large flexible products and so on, and thus have important developing and application prospects, such as in architectural, illumination and electricity generating areas. Therefore, many institutes and companies at home and abroad have paid much attention and investment on the organic solar batteries. However, so far the photoelectric conversion efficiency of the organic solar batteries is still much lower than the conventional inorganic solar batteries. Thus it is of great significance to develop new organic optoelectronic materials to improve the photoelectric conversion efficiency of the organic solar batteries and other semiconductor devices.

SUMMARY OF THE INVENTION

Therefore, a heterocyclic quinoid thiophene organic photoelectric material with wide spectrum response and good stability is provided, and a preparation method thereof with simple synthetic route and low cost is also provided.

A method for the applications of the hetercycloquinoid thiophene organic photoelectric material is provided in preparation of solar cell devices, organic field-effect transistors, organic electroluminescent devices, organic optical memory devices, organic nonlinear materials or organic laser devices.

A heterocyclic quinoid thiophene organic photoelectric material includes a compound represented by formula (1):

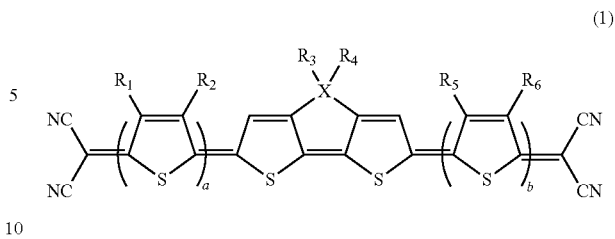

wherein, $R_1$, $R_2$, $R_5$ and $R_6$, which are identical or different, are H or $C_1$-$C_{20}$ alkyl or alkoxyl; $R_3$ and $R_4$, which are identical or different, are $C_1$-$C_{20}$ alkyl or alkoxyl; a and b, which are identical or different, are integer of 1-12; X is Si or C.

A preparation method of a heterocyclic quinoid thiophene organic photoelectric material includes the following steps: providing compounds A, B and C represented by following formulas, respectively, and malononitrile,

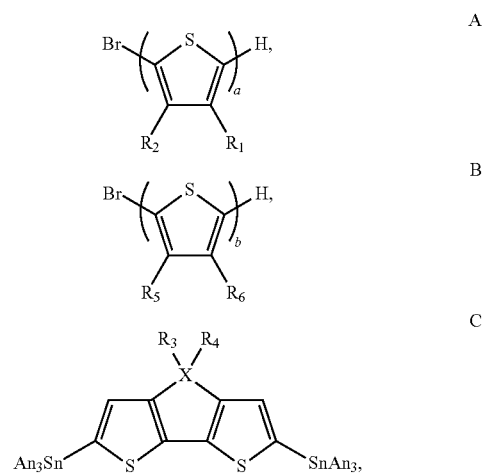

wherein, $R_1$, $R_2$, $R_5$ and $R_6$, which are identical or different, are H or $C_1$-$C_{20}$ alkyl or alkoxyl; $R_3$ and $R_4$, which are identical or different, are $C_1$-$C_{20}$ alkyl or alkoxyl; a and b, which are identical or different, are integer of 1-12; X is Si or C; An is $C_1$-$C_4$ alkyl;

carrying out a Stille coupling reaction using compounds A, B and C in the presence of a solvent and a catalyst;

carrying out a bromine substitution reaction using the product produced by the Stille coupling reaction to generate a brominated product;

carrying out a condensation reaction using the brominated product and the malononitrile in the presence of a solvent, a catalyst and a condensating agent to generate a compound represented by following formula (1):

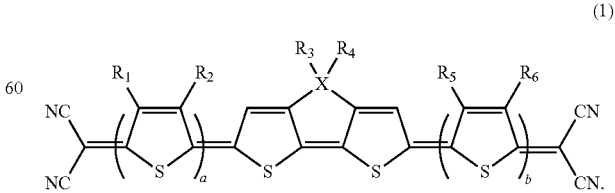

And, the heterocyclic quinoid thiophene organic photoelectric material is applied in preparation of solar cell devices, organic field-effect transistors, organic electroluminescent devices, organic optical memory devices, organic nonlinear materials or organic laser devices.

The heterocyclic quinoid thiophene organic photoelectric material mentioned above has a structure of multi-quinoid thiophene rings. As the thiophene ring is a five-membered ring and matches the Huckel's rule, the thiophene ring possesses advantages with moderated band gap, wide spectrum response, good heat stability and environmental stability. Moreover, by introducing two groups of dicyano ethylene (=C(CN)$_2$) which is a strong electron-withdrawing group at both ends of the molecular chain, the heterocyclic quinoid thiophene organic photoelectric material mentioned above turns into a quinoid thiophene structure with units of bithiophene joining with thiophene, such structure further widens the absorption range of the solar spectral, such as pushing the absorption band edge to the red and near infrared region, and thus increasing the photoelectric properties and the photoelectric conversion efficiency of the material. The preparation method of the heterocyclic quinoid thiophene organic photoelectric material mentioned above uses simple synthetic route and the Stille coupling reaction, which can simplify the preparation process and to reduce the preparation cost. When applying the said heterocyclic quinoid thiophene organic photoelectric material in preparation of solar cell devices, organic field-effect transistors, organic electroluminescent devices, organic optical memory devices, organic nonlinear materials or organic laser devices, the photoelectric and semiconductor properties of these devices are thus increased, the weight is reduced and it is convenient to prepare these devices in large quantities.

BRIEF DESCRIPTION OF THE DRAWINGS

The present disclosure will be described in detail with the following figures and embodiments, wherein.

DETAILED DESCRIPTION

Before describing the present invention in detail, it has to be understood that this invention is not limited to particular embodiments. It is also to be understood that the specific embodiments used herein are for the purpose of describing particular embodiments only, and are not intended to be limiting.

Figure 1:
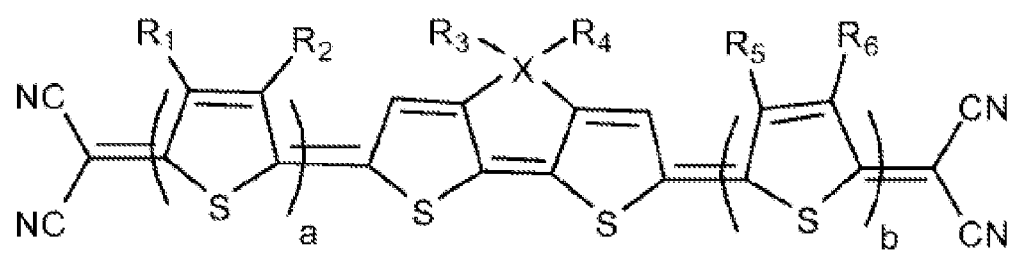
FIG. 1 shows a formula (1) of a heterocyclic quinoid thiophene organic photoelectric material according to one embodiment of the present disclosure.

Referring to FIG. 1, a formula (1) of a heterocyclic quinoid thiophene organic photoelectric material of an embodiment of the present disclosure is shown and the heterocyclic quinoid thiophene organic photoelectric material includes a compound represented by following formula (1):

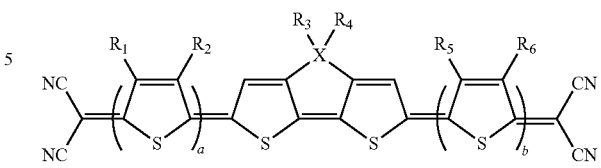

(1)

wherein, $R_1$, $R_2$, $R_5$ and $R_6$, which are identical or different, are H or $C_1$-$C_{20}$ alkyl or alkoxyl; $R_3$ and $R_4$, which are identical or different, are $C_1$-$C_{20}$ alkyl or alkoxyl; a and b, which are identical or different, are integer of 1-12; X is Si or C.

In one embodiment of the present disclosure, the heterocyclic quinoid thiophene organic photoelectric material has a symmetrical molecular structure. For example, the a and b are identical integer of 1-12, that is a=b. In a preferred embodiment, a=b=1 or 2, the molecular weight of such heterocyclic quinoid thiophene organic photoelectric material is small and a light weight of the product made by the material can be obtained. In one embodiment of the present disclosure, the $R_1$ and $R_6$, which are identical, are H or $C_1$-$C_{20}$ alkyl or alkoxyl, the $R_2$ and $R_5$, which are identical, are $C_1$-$C_{20}$ alkyl or alkoxyl, the $R_3$ and $R_4$, which are identical, are $C_1$-$C_{20}$ alkyl or alkoxyl. Such structure can simplify the preparation technology and reduce the cost. In a preferred embodiment of the present disclosure, the $R_1$, $R_2$, $R_5$ and $R_6$ are H, the $R_3$ and $R_4$ are $C_6$ alkyl or alkyl with more than 6 carbon atoms.

The heterocyclic quinoid thiophene organic photoelectric material mentioned above has a structure of multi-quinoid thiophene rings. As the thiophene ring is a five-membered ring and matches the Huckel's rule, the thiophene ring has a moderated band gap and a wide spectrum response, the wave band of which is about 300-750 nm which almost covers the visible light wave band. In addition, the organic photoelectric material also has good heat stability and environment stability and shows a good photoelectric property. Moreover, by introducing two groups of dicyano ethylene (=C(CN)$_2$) which is a strong electron-withdrawing group at both ends of the molecular chain, the photoelectric material turns into a quinoid thiophene structure with units of bithiophene joining with thiophene, such structure spreads the conjugated structure and increases the molecular planarity, which can reduce energy gap of the material, further widens the absorption range of the solar spectrum such as pushing the absorption band edge to the red and near infrared region, and thus increasing the photoelectric properties and the photoelectric conversion efficiency of the material. In addition, because the $R_3$ and $R_4$ are alkyl or alkoxyl, the solubility and molecular weight of the material can be increased, and such structure is benefit for the film process and further widens the application range of the material.

Figure 2:
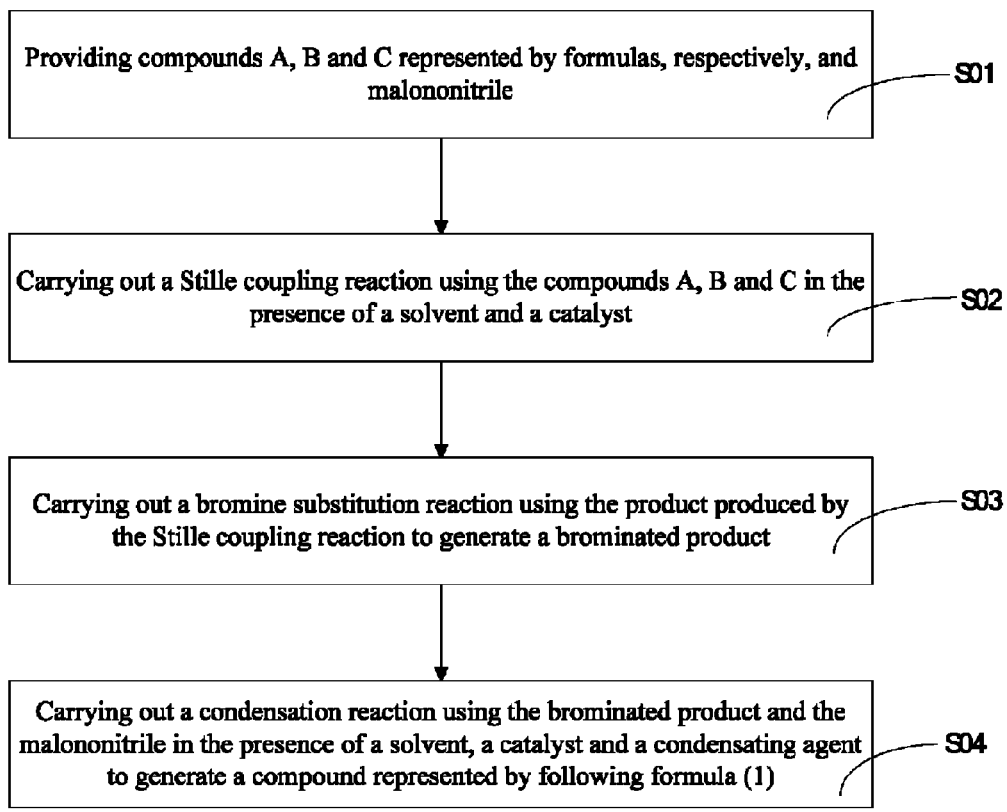
FIG. 2 shows a flow chart of a preparation method of a heterocyclic quinoid thiophene organic photoelectric material according to one embodiment of the present disclosure.

Referring to FIG. 2, a preparation method of the heterocyclic quinoid thiophene organic photoelectric material mentioned above includes the following steps:

S01: compounds A, B and C represented by following structural formulas and malononitrile are provided, respectively;

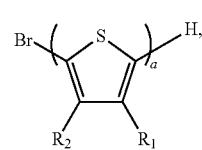

A

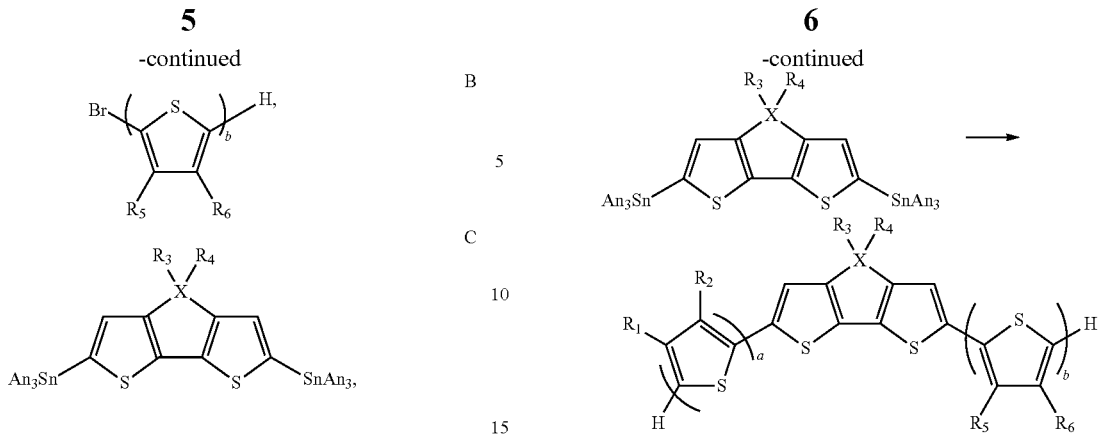

wherein, $R_1$, $R_2$, $R_5$ and $R_6$, which are identical or different, are H or $C_1$-$C_{20}$ alkyl or alkoxyl; $R_3$ and $R_4$, which are identical or different, are $C_1$-$C_{20}$ alkyl or alkoxyl; a and b, which are identical or different, are integer of 1-12; X is Si or C; An is $C_1$-$C_4$ alky.

S02: a Stille coupling reaction using the compounds A, B and C in the presence of a solvent and a catalyst is carried out;

S03: a bromine substitution reaction using product produced by the Stille coupling reaction is carried out to get a brominated product;

S04: a condensation reaction using the brominated product and the malononitrile in the presence of a solvent, a catalyst and a condensating agent is carried out to get a compound represented by following structural formula (1):

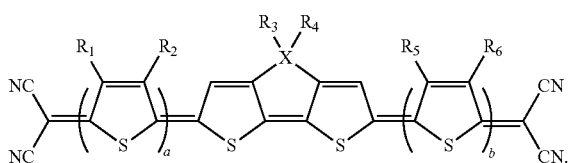 (1)

In step S01, the compounds A, B and C and the malononitrile may be purchased directly from the market or prepared by conventional methods, which will not be described in detail. The structures of the compounds A, B and C are in accordance with the heterocyclic quinoid thiophene organic photoelectric material mentioned above, which will not be described in detail. It should be noted that An may be $C_1$-$C_4$ alkyl, such as methyl, N-butyl or T-butyl.

In step S02, the catalyst of the Stille coupling reaction is organic palladium catalyst, for example, $Pd_2(dba)_3$/P(o-Tol)$_3$, $Pd(PPh_3)_4$ or $Pd(PPh_3)_2Cl_2$ and so on, and $Pd_2(dba)_3$/P(o-Tol)$_3$ is preferred. The solvent may be tetrahydrofuran (THF), methylene dichloride, glycol dimethyl ether, benzene or toluol and THF is preferred. The dosages of the compounds A, B and C may accord with the chemical reaction measurement, or the molar weights of the compounds A and B are overdose by 1%-20%, which is not limited to this. The reaction equation is shown as follows:

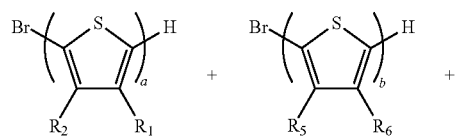

The specific implementation process of the step S02 includes the following steps: an anhydrous THF is added into a pressure pipe under $N_2$ atmosphere, the compounds A, B and C are added quickly, the organic palladium catalyst is added after the whole reaction system is bubbled for tens of minutes, then the pressure pipe is sealed, heated to 80° C. and refluxed for 24 hours. After the reaction is ended, a series of purification steps are carried out as follows: a KF aqueous solution (the concentration being, for example, 1.00 M) is added into the reaction products and the solution is stirred for tens of minutes, then a saturation sodium chloride aqueous solution is added, and the product is extracted using ethyl acetate, dried using anhydrous magnesium sulfate, rotary evaporated and separated using silica gel column chromatography.

In the Stille coupling reaction, when the a and b are different, the compound A and the compound B themselves will Stille couple with the compound C to form a compound with (2a+2) thiophene rings and a compound with (2b+2) thiophene rings, respectively. The yield of the target product in the reaction equation mentioned above is comparatively low and the target product of formula (1) may be purified following the purification steps mentioned above. It is to be understood that the compound with (2a+2) thiophene rings and the compound with (2b+2) thiophene rings can also be purified respectively, and they are also protected in the claimed structures of the present disclosure as organic optoelectronic materials with heterocyclic quinoid thiophene organic photoelectric material. When the a and b are identical, the compound A and the compound B is the same and the yield of the target compound is comparatively high.

In step S03, the solvent may be dimethyl formamide (DMF), THF, carbon tetrachloride ($CCl_4$), chloroform, dichloromethane or acetonitrile added with N-bromosuccinimide (NBS), $Br_2$, HBr or $PBr_3$, in which NBS is preferred. The reaction is shown referring to the following reaction equation:

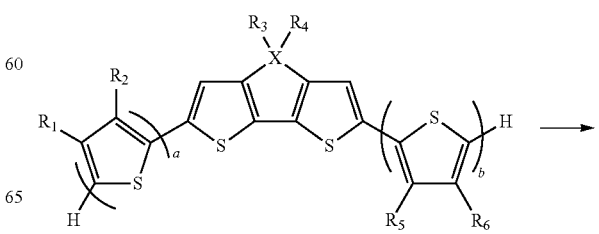

-continued

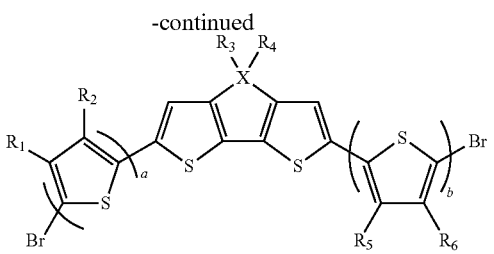

The specific implementation process includes the following steps: the NBS is added in batches into a reactor containing product generated in the step S02 and the DMF under ice-bath and dark condition and stirred for 12 hours at room temperature. When the reaction is over, the reaction solution is poured into ice-water to quench the reaction and is extracted by chloroform, dried by anhydrous magnesium sulfate, rotary evaporated and separated by silica gel column chromatography to obtain the product.

In the step S04, the catalyst is organic palladium catalyst such as $Pd_2(dba)_3/P(o\text{-}Tol)_3$, $Pd(PPh_3)_4$ or $Pd(PPh_3)_2Cl_2$, in which the $PdCl_2(PPh_3)_2$ is preferred. The solvent may be dimethoxyethane (DME), ethanol, dichloromethane, chloroform, THF, ethyl acetate, DMF, toluol or acetone, in which dimethoxyethane is preferred. The condensating agent may be sodium hydride or sodium alkoxide which may be sodium methoxide or sodium tert-butoxide, in which the sodium hydride is preferred. The reaction equation is shown as follows:

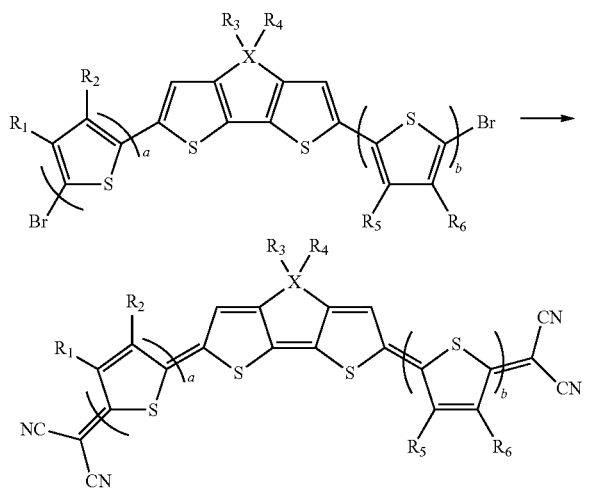

The specific implementation process includes the following steps: the malononitrile is added into a suspension containing sodium hydride (60% of which is in the oil) and DME under ice-bath condition, and then the reaction system is recovered to room temperature and stirred for 30 minutes. A brominated product obtained in the step S03 and the organic palladium catalyst are added, heated to reflux for 12 hours and then cooled to 0° C. A saturated $Br_2/H_2O$ solution and water are added successively and the reaction solution is pumping filtrated, water washed, dried and separated by silica gel column chromatography to obtain the product.

In the method of the heterocyclic quinoid thiophene organic photoelectric material mentioned above, the synthetic routes of the monomers A, B and C are comparatively simple and mature, thus the process and the cost are reduced.

In addition, the Stille coupling reaction is a mature coupling reaction with advantages of high productive rate, mild condition and easy to control, and moreover, by introduction of alkyl or alkoxy, the solubility of the product is improved which is benefit to widen the processability of the material.

The heterocyclic quinoid thiophene organic photoelectric material of this embodiment may be applied to various photoelectric or semiconductor devices such as the solar cell device, the organic field-effect transistor, the organic electroluminescent device, the organic optical memory device, the organic nonlinear material, the organic laser device and so on. Next, the solar cell device, the organic field-effect transistor and the organic electroluminescent device are taken as examples respectively to further illustrate the application of the material, other devices such as the optical memory device, the organic nonlinear material and the organic laser device which use the heterocyclic quinoid thiophene organic photoelectric material of this embodiment as their optical memory material, nonlinear material, laser material, semiconductor material and so on are similar with the below devices.

Figure 3:
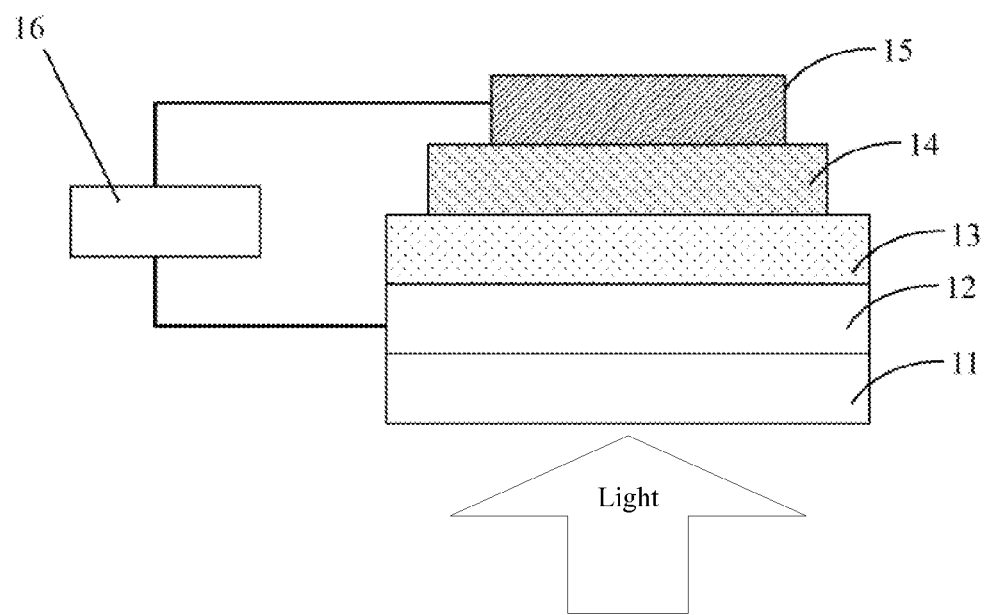
FIG. 3 is a schematic diagram of a solar cell device using a heterocyclic quinoid thiophene organic photoelectric material according to one embodiment of the present disclosure.

Referring to FIG. 3, a solar cell device with the heterocyclic quinoid thiophene organic photoelectric material of the above embodiment is shown and the solar cell device includes a glass base 11, a transparent anode 12, a middle auxiliary layer 13, an active layer 14 and a cathode 15, which are laminated in order. The middle auxiliary layer 13 uses polyethylene-dioxythiophene and polystyrene-sulfoacid composite material (hereafter may be referred as PEDOT: PSS). The active layer 14 includes electron donor material and electron acceptor material, the electron donor material uses the heterocyclic quinoid thiophene organic photoelectric material mentioned above and the electron acceptor material may be [6,6]phenyl-$C_{61}$-methyl butyrate (hereafter may be referred as PCBM). The transparent anode 12 may be indium tin oxide (hereafter may be referred as ITO) and the indium tin oxide whose sheet resistance is 10-20Ω/□ is preferred. The cathode 15 may be an aluminum electrode. The glass base 11 may be used as bottom layer and the ITO electrode is deposited on the glass base 11, then the middle auxiliary layer 13 is formed on the ITO electrode using oxide-plasma spray technique, the heterocyclic quinoid thiophene organic photoelectric material and the electron acceptor material are deposited on the middle auxiliary layer 13 using vacuum evaporation technique to form the active layer 14, and then the cathode 15 is deposited on the active layer 14 using vacuum evaporation technique to obtain the solar cell device mention above.

According to the FIG. 3, when under illumination, the light passes through the glass base 11 and the ITO electrode 12 and is absorbed by the heterocyclic quinoid thiophene organic photoelectric material of the active layer 14, thus producing excitons. These excitons move to the interface between the electron donor material and the electron acceptor material and transfer electrons to the electron acceptor material such as PCBM to implement separation of electric charges and thus free current carriers (free electrons and cavities) are formed. These free electrons are transferred to the cathode along the electron acceptor material and collected by the cathode and these free cavities are transferred to the anode along the electron donor material and collected by the anode, thus a photocurrent and a photovoltage are formed which implement transformation of the light and the electricity. When connected with a load 16, the solar cell device can supply power to the load 16. In such process, as the heterocyclic quinoid thiophene organic photoelectric material has a wide spectral response range, the material can fully use the light energy to acquire high photoelectric conversion efficiency and enhance the electrogenesis ability of the solar cell device. Moreover, such organic material can also reduce the weight of the solar cell device and may be prepared in large quantities using vacuum evaporation technique and so on.

Figure 4:
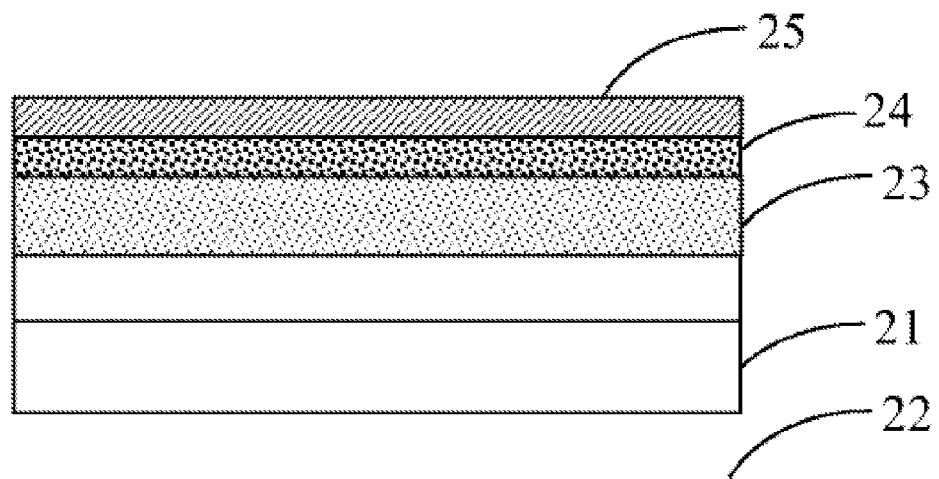
FIG. 4 is a schematic diagram of an organic electroluminescent device using a heterocyclic quinoid thiophene organic photoelectric material according to one embodiment of the present disclosure.

Referring to FIG. 4, an organic electroluminescent device using the heterocyclic quinoid thiophene organic photoelectric material of the above embodiment includes a glass base 21, a transparent anode 22, a light-emitting layer 23, a buffer layer 24 and a cathode 25, which are laminated in order. The transparent anode 22 may uses ITO, preferably the ITO having a sheet resistance of 10-20Ω/□□. The light-emitting layer 23 includes the heterocyclic quinoid thiophene organic photoelectric material of this embodiment. The buffer layer 24 may be but not limited to LiF. The cathode 25 may be Al or Ba but not limited to these materials. Therefore, in a specific embodiment, the structure of the organic electroluminescent device may be represented as ITO/the heterocyclic quinoid thiophene organic photoelectric material/LiF/Al. Each layer may be formed using conventional method except that the light-emitting layer is formed on the ITO using the vacuum evaporation technique.

Figure 5:
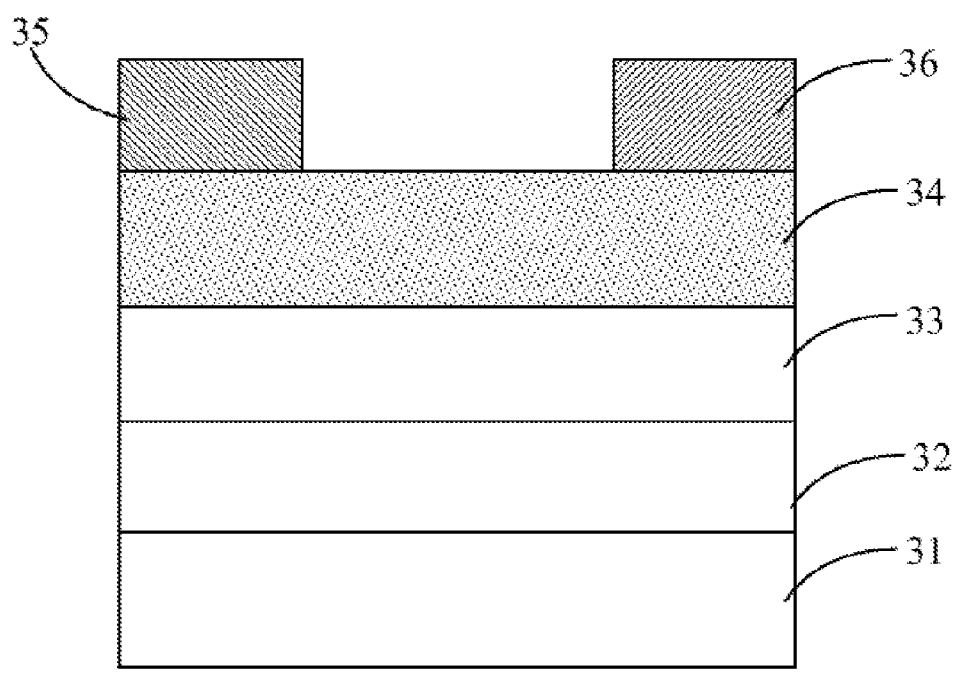
FIG. 5 is a schematic diagram of an organic field-effect transistor using a heterocyclic quinoid thiophene organic photoelectric material according to one embodiment of the present disclosure.

Referring to FIG. 5, an organic field-effect transistor using the heterocyclic quinoid thiophene organic photoelectric material of the above embodiment includes a substrate 31, an insulating layer 32, a modified layer 33, an organic semiconductor layer 34 and a source electrode 35 as well as a drain electrode 36 which are formed on the organic semiconductor layer 34, which are stacked on each other orderly. The substrate 31 may be but not limited to highly doped silicon. The insulating layer 32 may be but not limited to $SiO_2$ with a thickness among the micro-nano level, for example, 450 nm. The organic semiconductor layer 34 uses the above heterocyclic quinoid thiophene organic photoelectric material. The source electrode 35 and the drain electrode 36 may use but not limited to Au. The modified layer 33 may be but not limited to octadecyltrichlorosilane. The substrate 31, the insulating layer 32, the modified layer 33 and the source electrode 35 as well as the drain electrode 36 may be formed using conventional methods. The organic semiconductor layer 34 is formed using the heterocyclic quinoid thiophene organic photoelectric material of the above embodiment which is evaporated on the insulating layer 32 modified by the modified layer 33 in a vacuum environment whose vacuity is near $10^{-4}$ Pa.

The preparation method and the properties of the heterocyclic quinoid thiophene organic photoelectric material are shown in the following specific examples. The raw materials of the following examples may be prepared using known synthetic methods, for example, the raw material 4,4'-dihexyl-4H-cyclopentane[2,1-b:3,4-b']dithiophene may be prepared using 4H-cyclopentane[2,1-b:3,4-b']dithiophene and 1-bromohexane according to the reference: Macromolecules, 2007, 40, 1981; 4,4'-bis(2-ethyl-hexyl)-5,5' bis(trimethylsilyl)-dithiophene[3,2-b:2',3'-d]silane may be prepared using 3,3'-dibromo-5,5'-bis(trimethylsilyl)-2,2'-dithiophene and butyl lithium as well as dichiorodi (2-ethyl-hexyl)-silane according to the reference: J. Am. Chem. Soc., 2008, 130, 16144; 2,2'-di thiophene is prepared using 2-bromothiophene with $Ni(dppp)Cl_2$ catalyst according to the reference: J. Am. Chem. Soc., 1997, 119, 12568.

Example 1

The structure of a heterocyclic quinoid thiophene organic photoelectric material of the example 1 is:

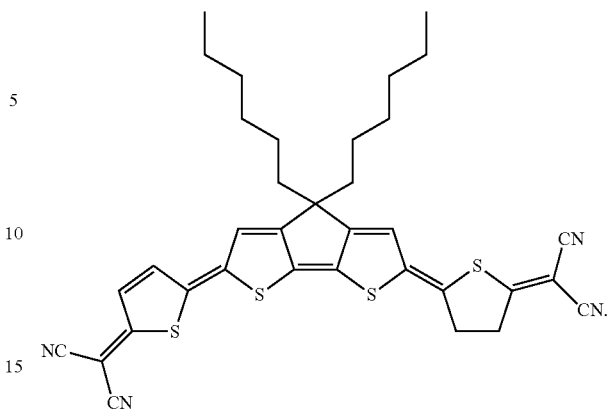

According to the formula, the heterocyclic quinoid thiophene organic photoelectric material of the example 1 has a symmetrical structure with four quinoid thiophenes and four cyano-groups. The $R_1$, $R_2$, $R_5$ and $R_6$ are H, the $R_3$ and $R_4$ are hexyl, $a=b=1$. The cyano-groups serve as electron-withdrawing groups. Such symmetrical structure results in good light absorption properties and photoelectric properties and small molecular weight of the heterocyclic quinoid thiophene organic photoelectric material, thus the weight of the product containing the material can be reduced.

The specific preparation process of the heterocyclic quinoid thiophene organic photoelectric material of the example 1 is shown as follows:

1) 4,4'-hexyl-2,6-dibromo-4H-cyclopenta[2,1-b:3,4-b'] dithiophene was prepared having a formula as:

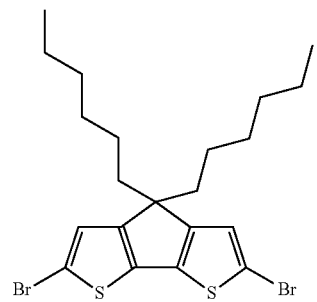

The specific preparation steps were as follows: 3.92 g of NBS was added in batches in a reaction flask containing 3.47 g of 4,4'-hexyl-4H-cyclopenta[2,1-b:3,4-b']dithiophene and 50 mL of DMF under ice-bath and dark conditions, then stirred for 12 hours at room temperature. After the reaction was over, the reaction solution was poured into ice-water to quench the reaction, extracted by ethyl acetate, dried by anhydrous sodium sulfate, rotary evaporated and separated by silica gel column chromatography to obtain the product.

The test result of the product was: MALDI-TOF-MS (m/z): 504.4 ($M^+$).

2) 4,4'-hexyl-2,2'-bis(trimethyl-tin-radical)-4H-cyclopenta[2,1-b:3,4-b']dithiophene as a compound C of this example was prepared having a formula as:

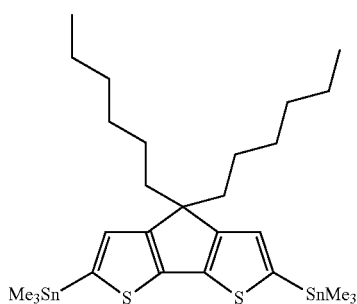

The specific preparation steps were as follows: 2.52 g of 4,4'-hexyl-2,6-dibromo-4H-cyclopenta[2,1-b:3,4-b']dithiophene and 40.0 mL of anhydrous THF solution were added into a reaction vessel, then 4.13 mL of n-butyl lithium solution (2.9 M hexane solution) was added into the reaction vessel in drops at −25° C. After stirred for 2 hours, 2.38 g of trimethyltin chloride was added in the reaction vessel and stirred for 6 hours. After the reaction was over, the reaction solution was recovered to room temperature, added with saturated ammonium chloride aqueous solution, extracted by diethyl ether, dried by anhydrous sodium sulfate, rotary evaporated and separated by silica gel column chromatography to obtain the product.

The test result of the product was: MALDI-TOF-MS (m/z): 672.2 (M$^+$).

3) 4,4'-hexyl-2,6-bis(thiophene thiophene 2-yl)-4H-cyclopenta[2,1-b:3,4-b']dithiophene was prepared with the following formula:

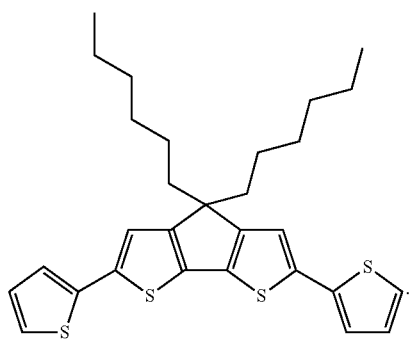 [SMILES: CCCCCCC1(CCCCCC)c2cc(-c3cccs3)sc2-c2sc(-c3cccs3)cc21]

In this step, that is the aforementioned step S02, on one respect, the source of the raw materials is simplified and thus the preparation process is simplified as well as the cost is reduced for that the compound A and the compound B is the same, and on another respect, the productive rate is higher compared with using of different the compound A and the compound B.

The specific preparation steps were as follows: 25 mL of anhydrous THF was added into a pressure pipe in N$_2$ atmosphere, then 2.02 g of 4,4'-hexyl-2,2'-bis(trimethyl-tin-radical)-4H-cyclopenta[2,1-b:3,4-b']dithiophene and 1.08 g of 2-bromothiophene was added quickly and 0.056 g of Pd$_2$(dba)$_3$ and 0.040 g of P(o-Tol)$_3$ was added after bubbling for 30 minutes. The pressure pipe was sealed and heated to 80° C. to reflux for 26 hours. After the reaction was over, 15.0 mL KF (1.00 M) aqueous solution was added and stirred for 30 minutes, then saturation aqueous sodium chloride solution was added and the whole system was extracted by ethyl acetate, dried by anhydrous magnesium sulfate, rotary evaporated and separated by silica gel column chromatography to obtain the product.

The test result of the product was: MALDI-TOF-MS (m/z): 510.9 (M$^+$).

4) 4,4'-hexyl-2,6-bis(5-bromo-thiophene-2-yl)-4H-cyclopenta[2,1-b:3,4-b']dithiophene was prepared having the following formula:

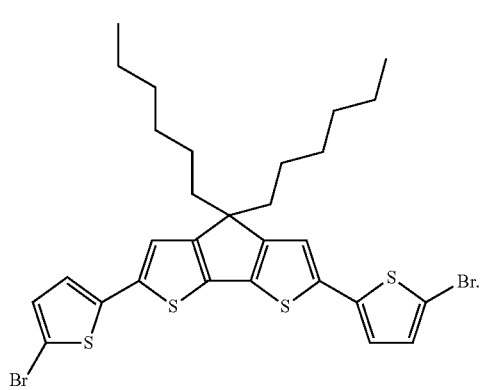 [SMILES: CCCCCCC1(CCCCCC)c2cc(-c3ccc(Br)s3)sc2-c2sc(-c3ccc(Br)s3)cc21]

The specific preparation steps were as follows: 0.78 g of NBS was added in batches in a reaction flask containing 1.02 g of 4,4'-hexyl-2,6-bis(thiophene 2-yl)-4H-cyclopenta[2,1-b:3,4-b']dithiophene and 20 mL of DMF under ice-bath and dark conditions and stirred at room temperature for 12 hours. After the reaction was over, the reaction solution was poured into ice-water to quench the reaction and extracted by chloroform, dried by anhydrous magnesium sulfate, rotary evaporated and separated by silica gel column chromatography to obtain the product.

The test result of the product was: MALDI-TOF-MS (m/z): 668.6 (M$^+$).

5) The final product whose structural formula was shown as above was prepared.

The specific preparation steps were as follows: 0.20 g of malononitrile was added in a suspension solution containing 0.24 g of sodium hydride (60% of which is in oil) and 20 mL of dimethoxyethane under ice-bath condition, then the whole system was recovered to room temperature, stirred for 30 minutes and added with 0.72 g of 2,6-bis(5-bromo-thiophene-2-yl)-dithieno[3,2-b:2',3'-d]thiophene and 0.038 g of PdCl$_2$(PPh$_3$)$_2$. The whole system was heated to reflux for 14 hours and then cooled to 0° C., added with saturated Br$_2$/H$_2$O solution. Water was added into the reaction system and the whole system was pumping filtrated, water washed, dried and separated by silica gel column chromatography to obtain the product.

The test result of the product was: MALDI-TOF-MS (m/z): 638.9 (M$^+$).

Example 2

The structure of a heterocyclic quinoid thiophene organic photoelectric material of the example 2 is:

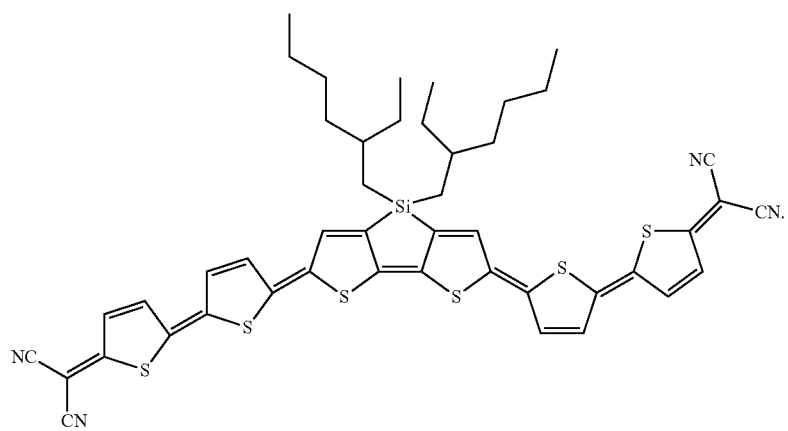 [SMILES: CCCCC(CC)C[Si]1(CC(CC)CCCC)c2c/c(=c3\cc/c(=c4\ccc(=C(C#N)C#N)s4)s3)sc2=c2s/c(=c3\cc/c(=c4\ccc(=C(C#N)C#N)s4)s3)cc21]

The formula of the heterocyclic quinoid thiophene organic photoelectric material is similar with the example 1 and has a symmetrical structure with six quinoid thiophene rings (that is a=b=2), in which the $R_1$, $R_2$, $R_5$ and $R_6$ are H, the $R_3$ and $R_4$ are 2-ethyl-hexyl which is different from the example 1 and the X is Si. The cyano-groups serve as electron-withdrawing groups. Such symmetrical structure implements good light absorption properties, good photoelectric properties of the hetercycloquinoid thiophene organic photoelectric material and so on.

The specific process of the preparation method of the heterocyclic quinoid thiophene organic photoelectric material of this example is shown as follows:

1) 5-bromo-2,2'-bithiophene as a compound A and a compound B of this example was prepared having the following formula:

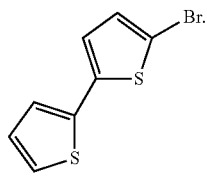 [SMILES: Brc1ccc(-c2cccs2)s1]

As the structure of the compound A and the structure of the compound B are identical, the compound A and the compound B may be prepared by step 2) only once, which simplifies the preparation processes and reduces the cost. In addition, if the structure of the heterocyclic quinoid thiophene organic photoelectric material is asymmetrical, that is the structure of the compound A and the structure of the compound B are different, then there will need twice step 2) respectively according to different raw materials.

The specific preparation steps were as follows: 17.80 g of NBS was added in batches into a reaction flask containing 16.60 g of 2,2'-bithiophene and 200 mL of DMF under ice-bath and dark conditions and stirred for 12 hours at room temperature. After the reaction was over, the reaction solution was poured into ice-water to quench the reaction, extracted by chloroform, dried by anhydrous magnesium sulfate, rotary evaporated and separated by silica gel column chromatography to obtain the product.

The test result of the product was: MALDI-TOF-MS (m/z): 245.2 ($M^+$).

2) 4,4'-bis(2-ethyl-hexyl)-5,5'-dibromo-dithieno[3,2-b:2',3'-d]silane was prepared having the following formula:

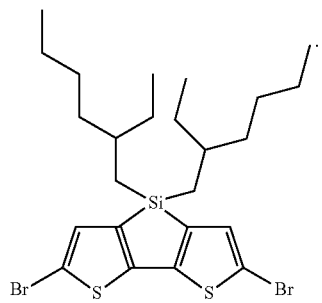 [SMILES: CCCCC(CC)C[Si]1(CC(CC)CCCC)c2cc(Br)sc2-c2sc(Br)cc21]

The specific preparation steps were as follows: 16.90 g of 4,4'-bis(2-ethyl-hexyl)-5,5'-bis(trimethylsilyl)-dithieno[3,2-b:2',3'-d]silane was added and dissolved in 200 mL of THF, then 11.00 g of NBS was added in batches and stirred for 6 hours at room temperature. After the reaction was over, the reaction solution was extracted by diethyl ether, dried by anhydrous sodium sulfate, pumping filtrated, rotary evaporated and separated by silica gel column chromatography to obtain the product.

The test result of the product was: MALDI-TOF-MS (m/z): 576.6 ($M^+$).

3) 4,4'-bis(2-ethyl-hexyl)-5,5'-bis(trimethyl tin)-dithieno[3,2-b:2',3'-d]silane as a compound C of this example was prepared having the following structural formula:

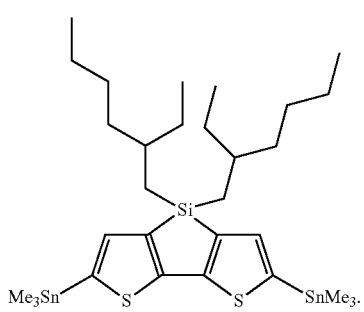

The specific preparation steps were as follows: 11.52 g of 4,4'-bis(2-ethyl-hexyl)-5,5'-dibromo-dithieno[3,2-b:2',3'-d]silane and 100.00 mL of anhydrous THF solution were added into the reaction flask and then 17.8 mL of n-butyl lithium solution (2.7 M n-hexane solution) was added in drops. After stirred for 2 hours, 9.71 g of trimethyltin chloride was added in drops and then stirred for 6 hours. After the reaction was over, the reaction solution was recovered to room temperature and added with saturated $NH_4Cl$ solution, extracted by diethyl ether, dried by anhydrous magnesium sulfate and rotary evaporated. At the end of this step there was no need to purify the product and might directly go to the next step.

The test result of the product was: MALDI-TOF-MS (m/z): 744.4 ($M^+$).

4) 2,6-bis(2,2'-bithiophene-5)-4,4'-bis(2-ethyl-hexyl)-dithieno[3,2-b:2',3'-d]silane was prepared having the following formula:

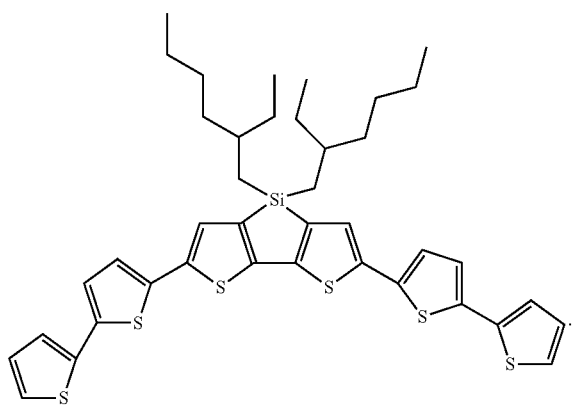 [SMILES: CCCCC(CC)C[Si]1(CC(CC)CCCC)c2cc(-c3ccc(-c4cccs4)s3)sc2-c2sc(-c3ccc(-c4cccs4)s3)cc21]

As the structure of the compound A and the structure of the compound B are identical which is similar with example 1, on one respect, the source of the raw materials is simplified and thus the preparation process is simplified as well as the cost is reduced, and on another respect, the productive rate is higher compared to the using of the compound A and the compound B which are different.

The specific preparation steps were as follows: 80 mL of anhydrous THF was added in a pressure pipe under a protection environment of nitrogen, then 7.44 g of 4,4'-bis(2-ethyl-hexyl)-5,5'-bis(trimethyl-tin)-dithieno[3,2-b:2',3'-d]silane and 5.40 g of 5-bromo-2,2'-bithiophene was added quickly and 0.19 g of $Pd_2(dba)_3$ and 0.14 g of $P(o-Tol)_3$ was added after bubbling for 30 minutes. The pressure pipe was sealed and heated to 80° C. to reflux for 24 hours. After the reaction was over, 30.0 mL KF (1.00 M) aqueous solution was added and stirred for 40 minutes, then saturation aqueous sodium chloride solution was added and the whole system is extracted by ethyl acetate, dried by anhydrous magnesium sulfate, rotary evaporated and separated by silica gel column chromatography to obtain the product.

The test result of the product was: MALDI-TOF-MS (m/z): 747.3 ($M^+$).

5) 2,6-bis(5'-bromo-2,2'-bithiophene-5)-4,4'-bis(2-ethyl-hexyl)-dithieno[3,2-b:2',3'-d]silane was prepared having the following structural formula:

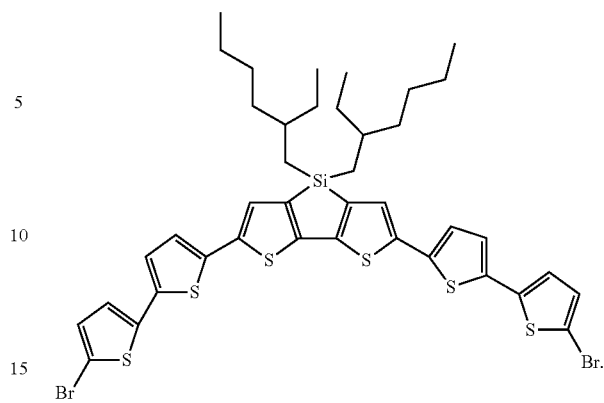

The specific preparation steps were as follows: 3.91 g of NBS was added in batches into a reaction flask containing 3.74 g of 2,6-bis(2,2'-bithiophene-5-yl)-4,4'-bis(2-ethyl-hexyl)-dithieno[3,2-b:2',3'-d]silane and 50 mL of DMF under ice-bath and dark conditions and stirred at room temperature for 12 hours. After the reaction was over, the reaction solution was poured into ice-water to quench the reaction and extracted by chloroform, dried by anhydrous magnesium sulfate, rotary evaporated and separated by silica gel column chromatography to obtain the product.

The test result of the product was: MALDI-TOF-MS (m/z): 905.1 ($M^+$).

6) The final product whose structural formula was shown as above was prepared.

The specific preparation steps were as follows: 0.16 g of malononitrile was added in a suspension solution containing 0.20 g of sodium hydride (60% of which is in oil) and 30 mL of dimethoxyethane under ice-bath condition, then the whole system was recovered to room temperature, stirred for 40 minutes and added with 1.81 g of 2,6-bis(5'-bromo-2,2'-dithiophene-5-yl)-4,4'-bis(2-ethyl-hexyl)-dithieno[3,2-b:2', 3'-d]silane and 0.070 g of $PdCl_2(PPh_3)_2$. The whole system was heated to reflux for 12 hours and then cooled to 0° C., added with saturated $Br_2/H_2O$ solution. Water was added in the reaction system and the whole system was pumping filtrated, water washed, dried and separated by silica gel column chromatography to obtain the product. The productive rate of the product is 61%.

The test result of the product was: MALDI-TOF-MS (m/z): 873.4 ($M^+$).

According to the above disclosure, the heterocyclic quinoid thiophene organic photoelectric material has a structure of multi-quinoid thiophene rings. As the thiophene ring is a five-membered ring and matches the Huckel's rule, the thiophene ring possesses advantages with moderated band gap, wide spectrum response, good heat stability and environmental stability. Moreover, by introducing two groups of dicyano ethylene (=$C(CN)_2$) which is a strong electron-withdrawing group at both ends of the molecular chain, the heterocyclic quinoid thiophene organic photoelectric material mentioned above turns into a quinoid thiophene structure with units of bithiophene joining with thiophene, such structure further widens the absorption range of the solar spectral such as pushing the absorption band edge to the red and near infrared region, and thus increasing the photoelectric properties and the photoelectric conversion efficiency of the material. The preparation method of the heterocyclic quinoid thiophene organic photoelectric material mentioned above uses simple synthetic route and the Stille coupling reaction, which can simplify the preparation process and to reduce the preparation cost. When applying the said heterocyclic quinoid thiophene organic photoelectric material in preparation of solar cell devices, organic field-effect transistors, organic electroluminescent devices, organic optical memory devices, organic nonlinear materials or organic laser devices, the photoelectric and semiconductor properties of these devices are thus increased, the weight is reduced and it is convenient to prepare these devices in large quantities.

Although the invention has been described in language specific to structural features and/or methodological acts, it is to be understood that the invention defined in the appended claims is not necessarily limited to the specific features or acts described. Rather, the specific features and acts are disclosed as sample forms of implementing the claimed invention.

What is claimed is:

1. A heterocyclic quinoid thiophene organic photoelectric material, comprising a compound represented by formula (1):

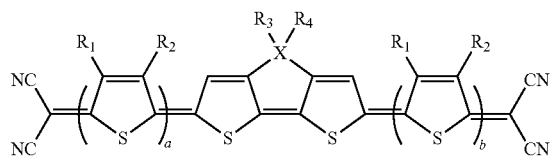

(1)

wherein $R_1$, $R_2$, $R_5$ and $R_6$, which are identical or different, are H or $C_1$-$C_{20}$ alkyl or alkoxyl; $R_3$ and $R_4$, which are identical or different, are $C_1$-$C_{20}$ alkyl or alkoxyl; a and b, which are identical or different, are integer of 1-12; X is Si or C.

2. The heterocyclic quinoid thiophene organic photoelectric material according to claim 1, wherein the $R_1$ and $R_6$, which are identical, are H or $C_1$-$C_{20}$ alkyl or alkoxyl; the $R_2$ and $R_5$, which are identical, are H or $C_1$-$C_{20}$ alkyl or alkoxyl; the $R_3$ and $R_4$, which are identical, are $C_1$-$C_{20}$ alkyl or alkoxyl.

3. The heterocyclic quinoid thiophene organic photoelectric material according to claim 1, wherein the a and b are identical integer of 1-12.

4. The heterocyclic quinoid thiophene organic photoelectric material according to claim 1, wherein the a and b are 1 or 2.

5. A preparation method of a heterocycloquinoid thiophene organic photoelectric material comprising the following steps:
providing compounds A, B and C represented by following formulas, respectively, and malononitrile,

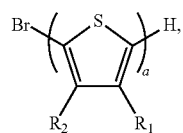

A

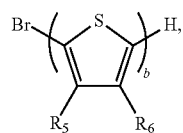

B

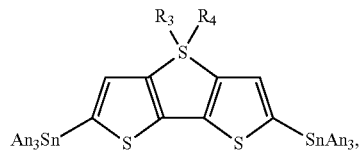

C wherein $R_1$, $R_2$, $R_5$ and $R_6$, which are identical or different, are H or $C_1$-$C_{20}$ alkyl or alkoxyl; $R_3$ and $R_4$, which are identical or different, are $C_1$-$C_{20}$ alkyl or alkoxyl; a and b, which are identical or different, are integer of 1-12; X is Si or C, An is $C_1$-$C_4$ alkyl;
carrying out a Stille coupling reaction using the compounds A, B and C in the presence of a solvent and a catalyst;
carrying out a bromine substitution reaction using the product produced by the Stille coupling reaction to generate a brominated product;
carrying out a condensation reaction using the brominated product and the malononitrile in the presence of a solvent, a catalyst and a condensating agent to generate a compound represented by following formula (1):

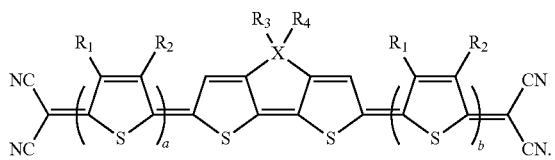

(1)

6. The preparation method of the heterocycloquinoid thiophene organic photoelectric material according to claim 5, further comprising purifying the product using silica gel column chromatography after the Stille coupling reaction, the bromine substitution reaction and the condensation reaction to obtain the coupling reaction product, the brominated product and the compound having the structural formula (1), respectively.

7. The preparation method of the heterocycloquinoid thiophene organic photoelectric material according to claim 5, wherein the bromine substitution reaction is carried out using the product of the Stille coupling reaction substitutional react with N-bromosuccinimide, $Br_2$, HBr or $PBr_3$ in the presence of a solvent of dimethylformamide, THF, $CCl_4$, chloroform, methylene dichloride or acetonitrile.

8. The preparation method of the heterocycloquinoid thiophene organic photoelectric material according to claim 5, wherein the catalyst of the condensation reaction is organic palladium catalyst and the solvent is dimethoxyethane, ethanol, methanol, dichloromethane, chloroform, tetrahydrofuran, ethyl acetate, DMF, toluene or acetone.

9. The preparation method of the heterocycloquinoid thiophene organic photoelectric material according to claim 5, the catalyst of the Stille coupling reaction is organic palladium catalyst, the solvent is tetrahydrofuran, dichloromethane, dimethoxyethane, ether or toluene, and the condensating agent is sodium hydride or sodium alkoxide.

10. A method for the applications of the heterocycloquinoid thiophene organic photoelectric material according to claim 1 in preparation of solar cell devices, organic field-effect transistors, organic electroluminescent devices, organic optical memory devices, organic nonlinear materials or organic laser devices.

11. A method for the applications of the heterocycloquinoid thiophene organic photoelectric material according to claim 2 in preparation of solar cell devices, organic field-effect transistors, organic electroluminescent devices, organic optical memory devices, organic nonlinear materials or organic laser devices.

12. A method for the applications of the heterocycloquinoid thiophene organic photoelectric material according to claim 3 in preparation of solar cell devices, organic field-effect transistors, organic electroluminescent devices, organic optical memory devices, organic nonlinear materials or organic laser devices.

13. A method for the applications of the heterocycloquinoid thiophene organic photoelectric material according to claim 4 in preparation of solar cell devices, organic field-effect transistors, organic electroluminescent devices, organic optical memory devices, organic nonlinear materials or organic laser devices.

* * * * *